US011393562B2

(12) United States Patent
Andry et al.

(10) Patent No.: US 11,393,562 B2
(45) Date of Patent: Jul. 19, 2022

(54) DEVICE, SYSTEM, AND METHOD FOR OPERATIVE PERSONAL HEALTH RECORDS

(71) Applicant: KONINKLIJKE PHILIPS N.V., Eindhoven (NL)

(72) Inventors: Francois Andry, Paris (FR); Carla-Krystin Andrade, San Francisco, CA (US); John Corydon Huffman, Portland, OR (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 419 days.

(21) Appl. No.: 15/995,159

(22) Filed: Jun. 1, 2018

(65) Prior Publication Data
US 2018/0358115 A1 Dec. 13, 2018

Related U.S. Application Data

(60) Provisional application No. 62/516,127, filed on Jun. 7, 2017.

(51) Int. Cl.
*H04L 12/18* (2006.01)
*G16H 10/60* (2018.01)
(Continued)

(52) U.S. Cl.
CPC ............ *G16H 10/60* (2018.01); *G06F 21/62* (2013.01); *G16H 15/00* (2018.01); *G16H 80/00* (2018.01); *H04L 63/08* (2013.01)

(58) Field of Classification Search
CPC ........ G06F 21/62; G16H 10/60; G16H 15/00; G16H 80/00; H04L 63/08
See application file for complete search history.

(56) References Cited

U.S. PATENT DOCUMENTS

2006/0229918 A1* 10/2006 Fotsch .................. G06Q 50/22
 705/3
2007/0260492 A1* 11/2007 Feied ..................... G16H 10/60
 705/3
(Continued)

OTHER PUBLICATIONS

Kikuchi, S. et al., Applying cloud computing model in PHR architecture, Proceedings of the 2012 Joint International Conference on Human-Centered Computer Environments, pp. 236-237, ACM New York, NY, 2012.
(Continued)

*Primary Examiner* — Maroun P Kanaan (57) ABSTRACT

A device, system, and method creates an operative personal health record (PHR). The PHR server maintains the PHR of an owner, the PHR including a plurality of sections, one of the sections being an aggregated section including a plurality of subsections, one of the subsections corresponding to a health care entity. The method includes receiving a retrieval input from the owner of the PHR, the retrieval input identifying the health care entity from which information is to be requested. The method includes generating a request for the information. The method includes transmitting the request to the health care entity. The method includes receiving the information from the health care entity. The method includes including the information in the subsection of the aggregated section in the PHR corresponding to the health care entity.

17 Claims, 4 Drawing Sheets

(51) Int. Cl.
*G16H 15/00* (2018.01)
*H04L 9/40* (2022.01)
*G06F 21/62* (2013.01)
*G16H 80/00* (2018.01)

(56) References Cited

U.S. PATENT DOCUMENTS

| | | |
|---|---|---|
| 2008/0133273 A1 | 6/2008 | Marshall |
| 2009/0080408 A1* | 3/2009 | Natoli .................. H04L 67/327 370/351 |
| 2012/0172724 A1 | 7/2012 | Hill et al. |
| 2012/0215560 A1* | 8/2012 | Ofek ...................... G16H 10/60 705/3 |
| 2012/0232929 A1* | 9/2012 | Experton ............... G16H 10/65 705/3 |
| 2013/0237811 A1 | 9/2013 | Mihailescu et al. |
| 2013/0324841 A1 | 12/2013 | Kamen et al. |
| 2015/0080705 A1 | 3/2015 | Illkka et al. |
| 2015/0178449 A1* | 6/2015 | Ferry ...................... G06F 19/00 705/3 |
| 2015/0213194 A1* | 7/2015 | Wolf .................. G06K 9/00442 705/3 |
| 2015/0261917 A1* | 9/2015 | Smith .................... G06F 19/321 705/3 |
| 2016/0232306 A1* | 8/2016 | Achan ................. G06F 21/6245 |
| 2018/0011973 A1* | 1/2018 | Fish ..................... A61B 5/1171 |

OTHER PUBLICATIONS

Balinsky, H. et al., Fine Grained Access of Interactive Personal Health Records, DocEng '15 Proceedings of the 2015 ACM Symposium on Document Engineering, Abstract.

* cited by examiner

DEVICE, SYSTEM, AND METHOD FOR OPERATIVE PERSONAL HEALTH RECORDS

BACKGROUND INFORMATION

A personal health record (PHR) may include health information and other related information associated with an individual (collectively referred herein as "health related information"). The PHR may be owned, maintained, and managed by the individual (hereinafter "owner") in a personal way such that the health related information is managed in a private, secure, and confidential manner. If the owner of the PHR is vigilant with updating the PHR, the PHR may be used to provide an encompassing summary of an entire medical history of the owner. The PHR may include information from a variety of different sources including from the owner, a health care provider, a health care organization, etc. The information may be manually added to the PHR by the owner, may be automatically added by a service providing the PHR, or a combination thereof. For example, the service providing the PHR may receive manual entries or inputs from the owner, may request information from the health care provider, may passively collect health related information from an electronic device of the owner, etc.

The PHR may be utilized in various formats. In a simple format, the PHR may be a paper record kept by the owner. However, as a paper record, the PHR may not be readily available when needed such as during a consultation with a health care provider. In another format, the PHR may be in an electronic format. In a first example, the PHR in the electronic format may be kept in a substantially similar manner as the paper record in which the health related information is stored on a personal file of the owner. If the personal file is stored on a cloud or through an online mechanism, the PHR may be accessible in an online manner. In a second example, the PHR in the electronic format may be provided by a service such as an online service (e.g., a website). In this manner, the PHR may be accessible online so long as the online service can be reached.

The PHR may include a variety of different types of health related information. For example, the health related information may include personal information such as birth date, address, contact number(s), emergency contact, emergency contact number, etc. In another example, the health related information may be directed to medical topics such as primary care physician information, any specialist information, blood type, allergies, reactions to medication, chronic diseases, family history, past illnesses, past hospitalizations, imaging reports, laboratory test results, current or past medications with corresponding doses and length of use, prescription record, past surgeries or other procedures, vaccination history, booster history, dates of physicals/tests/ screenings, etc. In a further example, the health related information may include legal information such as a living will, advance directives, etc. In yet another example, the health related information may include activity information of the owner such as an exercise regiment and dietary habits as well as health goals or care plans.

When the PHR is kept in an electronic format, the health related information may be separated into publicly available information and private information. For example, the personal information may be categorized as private information. However, the personal information may also be divided into sections that are categorized as private information (e.g., home information) and public information (e.g., emergency contact number). The other types of information may also be categorized in this manner. For example, when the health related information is received from a health care provider, this information may be categorized as public information. It is noted that being publicly available may refer to being accessible by health care providers and health care organizations.

When the PHR is in the paper format or in a personal file in the electronic format, the health related information in the PHR may be stored using any user preferred manner. When the PHR is provided by a service in the electronic format, the health related information in the PHR may be stored or displayed according to the manner selected by the service. For example, the service may determine which of the information of the PHR is to be publicly available or private. In another example, the service may arrange the information according to a standard the service has selected such as a personal information page, a general health information page, a medication page, etc.

In view of the encompassing summary that may be included in the PHR, there may be benefits of having a most current PHR. However, maintaining and updating the PHR to be comprehensive requires significant time and resources. For example, the owner may take it upon him/herself to use his/her own time and resources to update the PHR. Accordingly, the owner may contact a health care provider to collect and enter results of a procedure or exam performed by the health care provider. In another example, to be current, the owner may update the PHR each time a health related event has occurred (e.g., each time a doctor is visited, each time a prescription is filled, each time a test is performed, each visit to a hospital, etc.).

Despite the potential importance of having a current PHR that is available for use by health care providers and health care organizations (hereinafter collectively referred to as "health care entity"), the management and updating of the PHR is limited to the above described manner. Unfortunately, health care entities (e.g., doctors, hospitals, pharmacies, insurance companies, etc.) have not adopted a universal manner of using information technology to cooperate in maintaining a current PHR for the owner. In fact, there may only be select health care entities (e.g., a small minority) who are even capable of transmitting information in an electronic manner for the PHR to be updated.

The information received from a health care entity may be based on an electronic health record (EHR). The EHR is an entirely separate record from the PHR since the EHR is owned and operated by the health care entity (e.g., institutions such as hospitals) and includes data entered by users associated with the health care entity (e.g., clinicians) or other information related to procedures associated with the individual patient (e.g., billing data to support insurance claims). Thus, the health care entity owns, operates, manages, and updates the EHR for their own records pertaining to a specific individual patient. Although the EHR may potentially be shared among health care entities, there is no manner of properly incorporating the EHR into the PHR. Instead, when information is requested from the health care entity, a file including pertinent information for the owner as selected by the health care entity is provided and the PHR is updated with this information.

In a particular manner of implementing the PHR, a consensus model is where the health related information belongs to the patient and not the health care entity who may have generated the data. The health related information may be stored with various encryptions for privacy purposes. The management functions of the health related information may be realized via a Service Oriented Architecture (SOA) and exposed as a health care specific Platform as a Service (PaaS) layer. A fine-grained access control may be incorporated to enable multiple people to have differential access to the PHR and the health related information. In this consensus model, the minimum PHR capabilities may include a self-contained tamper proof digital bundle, be persistent and accessible by its owner anytime and from anywhere, have sensitive or private information to always remain under the firm control of the owner of the PHR without the need for a trusted third party, provide suitable mechanisms for access, and allow the owner to share only partial versions of the PHR if needed.

Under the consensus model and other models of the PHR using conventional technologies, all of the health related information included in the PHR is stored in the same record. Therefore, even with all of the above features of the consensus model, the owner of the PHR or the owner to which the health related information pertains must control and manage how the information is to be separated or organized in the PHR for the features to be realized. Accordingly, the PHR is limited in options and features and requires a significant contribution from the owner of the PHR.

Furthermore, the health related information in the PHR is sensitive information where privacy concerns are considered. Therefore, the health related information of the PHR is not generally publicly available to access, especially when the PHR is in an electronic format. Even if the PHR is to be accessed by a health care entity, the entire contents of the health related information may become accessible with the conventional features of the PHR. When the entire contents of the health related information becomes available to a health care entity, the EHR maintained for the owner by the health care entity may now include this information. From the side of the health care entity, those skilled in the art will understand that various privacy regulations have been established such as with the Health Insurance Portability and Accountability Act of 1996 (HIPAA) where an individual's health related information and its use/disclosure must adhere to the standards included in HIPAA. Thus, maintaining a level of privacy in the PHR from the public and health care entities provide an important feature. However, the current state of PHRs do not allow for a selective accessibility of identified portions in the PHR.

SUMMARY

The exemplary embodiments are directed to a method, comprising: at a personal health record (PHR) server maintaining a PHR of an owner, the PHR including a plurality of sections, one of the sections being an aggregated section including a plurality of subsections, one of the subsections corresponding to a health care entity: receiving a retrieval input from the owner of the PHR, the retrieval input identifying the health care entity from which information is to be requested; generating a request for the information; transmitting the request to the health care entity; receiving the information from the health care entity; and including the information in the subsection of the aggregated section in the PHR corresponding to the health care entity.

The exemplary embodiments are directed to a personal health record (PHR) server maintaining a PHR of an owner, comprising: a transceiver communicating via a communications network, the transceiver configured to exchange data with a user device utilized by the owner of the PHR and an electronic device of a health care entity; a memory storing an executable program; and a processor that executes the executable program that causes the processor to perform operations in maintaining the PHR, the PHR including a plurality of sections, a first one of the sections being a personal section including personal information associated with the owner, a second one of the sections being an aggregated section including a plurality of subsections, each of the subsections corresponding to a respective health care entity, the subsections including respective health related information associated with the owner based on a respective record maintained by the respective health care entity.

The exemplary embodiments are directed to a personal health record (PHR) server maintaining a PHR of an owner, the PHR including a plurality of sections, one of the sections being an aggregated section including a plurality of subsections, one of the subsections corresponding to a health care entity, comprising: a transceiver communicating via a communications network, the transceiver configured to exchange data with a user device utilized by the owner of the PHR and an electronic device of a health care entity; a memory storing an executable program; and a processor that executes the executable program that causes the processor to perform operations, comprising: receiving a retrieval input from the owner of the PHR, the retrieval input identifying the health care entity from which information is to be requested; generating a request for the information; transmitting the request to the health care entity; receiving the information from the health care entity; and including the information in the subsection of the aggregated section in the PHR corresponding to the health care entity.

DETAILED DESCRIPTION

The exemplary embodiments may be further understood with reference to the following description and the related appended drawings, wherein like elements are provided with the same reference numerals. The exemplary embodiments are related to a device, a system, and a method for generating an operative personal health record (PHR) that provides various features and operations for health related information to be managed and updated in the PHR. Specifically, the exemplary embodiments provide a first mechanism in which health related information is added to the PHR and a second mechanism in which health related information from the PHR is transmitted to a requestor. As will be described in further detail below, the manner in which the health related information is stored and organized may be used in performing the first and second mechanisms.

The exemplary embodiments are configured to clearly separate the health related information based on whether the health related information was initially created by the owner of the PHR or whether the health related information was initially created by a health care entity (e.g., health care provider, health care organization, etc.) or based on an electronic health record (EHR) belonging to the health care entity. Specifically, the health related information of the PHR may be separated into a plurality of sections: a first section for personal information associated with the owner, a second section associated with aggregated data from health care entities, a third section for selectively viewable information, etc. By organizing the health related information according to the exemplary embodiments, the exemplary embodiments may also provide a way for each party (e.g., the owner of the PHR, the health care entity, or a third party) to add and/or access corresponding selections of the health related information based on an access control and policies implemented to the organization of the PHR. Therefore, the exemplary embodiments include an architecture that provides a finer grain access as well as a sharing and a delegation of the health related information in the PHR.

Figure 1:
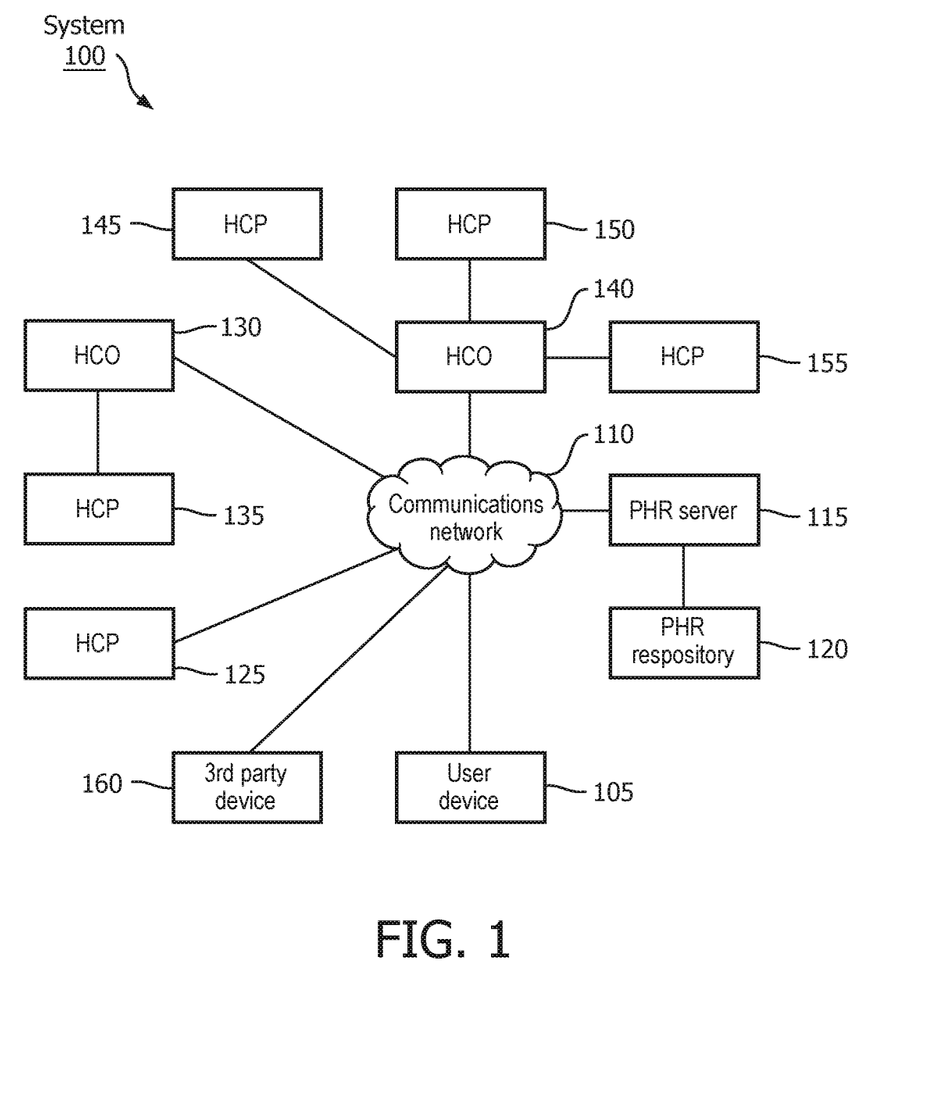
FIG. 1 shows a system according to the exemplary embodiments.

FIG. 1 shows a system 100 according to the exemplary embodiments. The system 100 relates to a communication between various components involved in utilizing a PHR, both in updating the PHR to a most current state and requesting information from the PHR. The system 100 may include a user device 105, a communications network 110, and a plurality of devices associated with different health care entities. For example, a first health care entity may include a health care provider (HCP) 125, a second health care entity may include a health care organization (HCO) 130 that includes at least a HCP 135, and a third health care entity may include a HCO 140 that includes at least three HCPs 145, 150, 155. As will be described in further detail below, the system 100 is configured to add health related information into the PHR from information provided by the user device 105 and/or the health care entities as well as transmit requested health related information from the PHR to the requesting health care entity. The system 100 may further include a third party device 160. The third party device 160 may also request for health related information from the PHR but is unassociated with a health care entity (e.g., a device used by a relative of the owner). Accordingly, to provide these functionalities, the system 100 may also include a PHR server 115 and a PHR repository 120.

The user device 105 may be any electronic device that is used by an individual who owns the PHR (hereinafter "owner"). For example, the user device 105 may be a desktop computer, a laptop computer, a mobile phone, a tablet computer, a smartphone, a phablet, an embedded device, a wearable, etc. The user device 105 may include all the hardware, software, and firmware for operations and functionalities associated with the PHR including those of the exemplary embodiments to be used (e.g., a processor, a memory, a display device, a transceiver, etc.). Accordingly, the user device 105 may be configured to execute an application that allows the PHR to be accessed and the features of the PHR to be used. For example, the application may be a proprietary PHR application that establishes a connection to the PHR server 115. In another example, the application may be a browser application in which an online service or webpage of the PHR server 115 is accessed.

The user device 105 may also be configured to establish a connection with the communications network 110. For illustrative purposes, the exemplary embodiments are described herein where the PHR is a service provided by the PHR server 115. Accordingly, data may be exchanged between the user device 105 and the PHR server 115 such that the PHR server 115 may provide the PHR service. However, it is noted that this implementation is only exemplary. The PHR and a corresponding PHR application may operate locally on the user device 105. A further service or third party relay may be used for the PHR to become available via the communications network 110.

The communications network 110 may be configured to communicatively connect the various components of the system 100 to exchange data. Specifically, the communications network 110 may be used to exchange data between the PHR server 115 and the user device 105 as well as between the PHR server 115 and the health care entities (e.g., the HCP 125, the HCO 130, and the HCO 140). The communications network 110 may represent any single or plurality of networks used by the components of the system 100 to communicate with one another. For example, the HCO 140 may utilize a private network such that the communications network 110 may be communicatively connected to the private network. It should be noted that the communications network 110 and all networks that may be included therein may be any type of network. For example, the communications network 110 may be a local area network (LAN), a wide area network (WAN), a virtual LAN (VLAN), a WiFi network, a HotSpot, a cellular network (e.g., 3G, 4G, Long Term Evolution (LTE), etc.), a cloud network, a wired form of these networks, a wireless form of these networks, a combined wired/wireless form of these networks, etc.

The health care entities including the HCOs 130, 140 and the HCPs 125, 135, 145, 150, 155 may include any type of health care practitioner. For example, the HCP 125 (as well as the HCPs 135, 145, 150, 155) may be utilized by a physician, a specialist, a technician, etc. The HCP 125 may represent any electronic device that is configured to perform the functionalities associated with the health care practitioner. The HCP 125 may also be any type of electronic device such as those noted above for the user device 105. Furthermore, the HCP 125 may include the necessary hardware, software, and/or firmware to perform the various operations associated with the health care practitioner including any medical treatments. The HCP 125 may further include the required connectivity hardware, software, and firmware (e.g., transceiver) to establish a connection with the communications network 110 to further establish a connection with the PHR server 115 of the system 100. It is again noted that the description of the HCP 125 may also apply to the HCPs 135, 145, 150, 155.

The HCOs 130, 140 may include one or more HCPs. As illustrated, the HCO 130 may include one HCP 135 while the HCO 140 may include more than one HCP 145, 150, 155. However, it is noted that the HCOs 130, 140 including the number of HCPs illustrated in the system 100 of FIG. 1 is only exemplary. Those skilled in the art will understand that the HCOs 130, 140 may include any number of HCPs. The HCOs 130, 140 may represent any organization which HCPs may be associated. For example, the HCOs 130, 140 may be a health maintenance organization (HMO). In another example, the HCOs 130, 140 may be part of a practice group. In a further example, the HCOs 130, 140 may be a hospital. In yet another example, the HCOs 130, 140 may be part of a health insurance organization.

The health care entities (both HCPs and HCOs) may be capable of generating and maintaining respective electronic health records (EHRs). The EHRs may be stored on respective repositories (not shown). For example, the HCP 125 may not be part of a HCO and thus store the EHRs of patients on a local or remote repository. In another example, the HCOs 130, 140 may include a respective network repository on a corresponding private network (not shown) of the HCOs 130, 140. In this manner, the EHRs of patients of HCPs may be owned, operated, managed, and maintained by the respective HCP and/or the HCO that the HCP is associated. For example, the HCP 125 may have an EHR for a patient corresponding to the owner using the user device

105. This EHR may be proprietary to the HCP 125 only. In another example, the HCO 140 may have an EHR for the patient corresponding to the owner using the user device 105. This EHR may be proprietary to the HCO 140 such that the HCPs 145, 150, 155 may have access to this EHR.

It is noted that the HCPs 125, 135, 145, 150, 155 may be electronic devices that are used by the health care practitioner in a variety of different manners. For example, the HCPs may be professional devices in which documentation functionalities are performed. In this manner, the documents being created may be incorporated into the EHRs. In another example, the HCPs may be procedure devices such as for image capturing, image interpretation, lab tests, etc. When the procedures are performed, a corresponding document may be created to be incorporated into the EHRs.

The PHR server 115 may be a component of the system 100 that performs functionalities associated with managing information flow of the PHR for the owner of the PHR (e.g., user of the user device 105). The PHR server 115 may further be configured to provide further features to automate operations in updating the PHR. For example, the PHR server 115 may subscribe the PHR to feeds from health care providers that enable an automatic update of the PHR based on information provided by the health care providers. Therefore, whenever the owner of the PHR receives a health care update (e.g., from a health care provider), the result may be automatically entered into the PHR. In a third example, a combination of a manual approach and an automated approach may be used to update the PHR. As will be described in further detail below, in the first mechanism, the PHR server 115 may receive inputs instructing how the PHR is to be maintained, managed, and/or updated. The inputs may also instruct the PHR server 115 to retrieve information. In the second mechanism, the PHR server 115 may also receive requests from the health care entities or the third party device 160, verify the request, and transmit the requested information when authorized. For illustrative purposes, the exemplary embodiments described herein relate to requests from the health care entities. However, the exemplary embodiments may also be used for requests from the third party device 160.

The PHR repository 120 may represent any source from which PHRs are stored for use by the PHR server 115. As noted above, the system 100 may include a plurality of user devices having respective users who may be patients of the health care entities. The users may also have respective PHRs (e.g., be owners of PHRs) and utilize the service provided by the PHR server 115. These PHRs may therefore be stored in the PHR repository 120. Among the PHRs that are stored, the PHR for the owner using the user device 105 may be stored in the PHR repository 120. In a particular implementation, the PHR repository 120 may be used by the PHR server 115 to provide a cloud based PHR tenant storage structure.

It is noted that the system 100 including only the user device 105 is only exemplary. The system 100 may represent the health care entities to which the owner using the user device 105 may be associated or has had health care related experiences. For example, the owner using the user device 105 may have visited the HCP 125, the HCP 135 and at least one of the HCPs 145, 150, 155. Accordingly, the health care entities shown in the system 100 may have the owner using the user device 105 as a patient and is maintaining an EHR for this owner. However, an overall representation of the system 100 may include a plurality of different user devices having respective users. Each user may also have experiences with one or more HCPs such that each of these users have a respective EHR being maintained by their HCPs. Accordingly, the system 100 may also include further health care entities, some of which may overlap among different patients/users.

Figure 2:
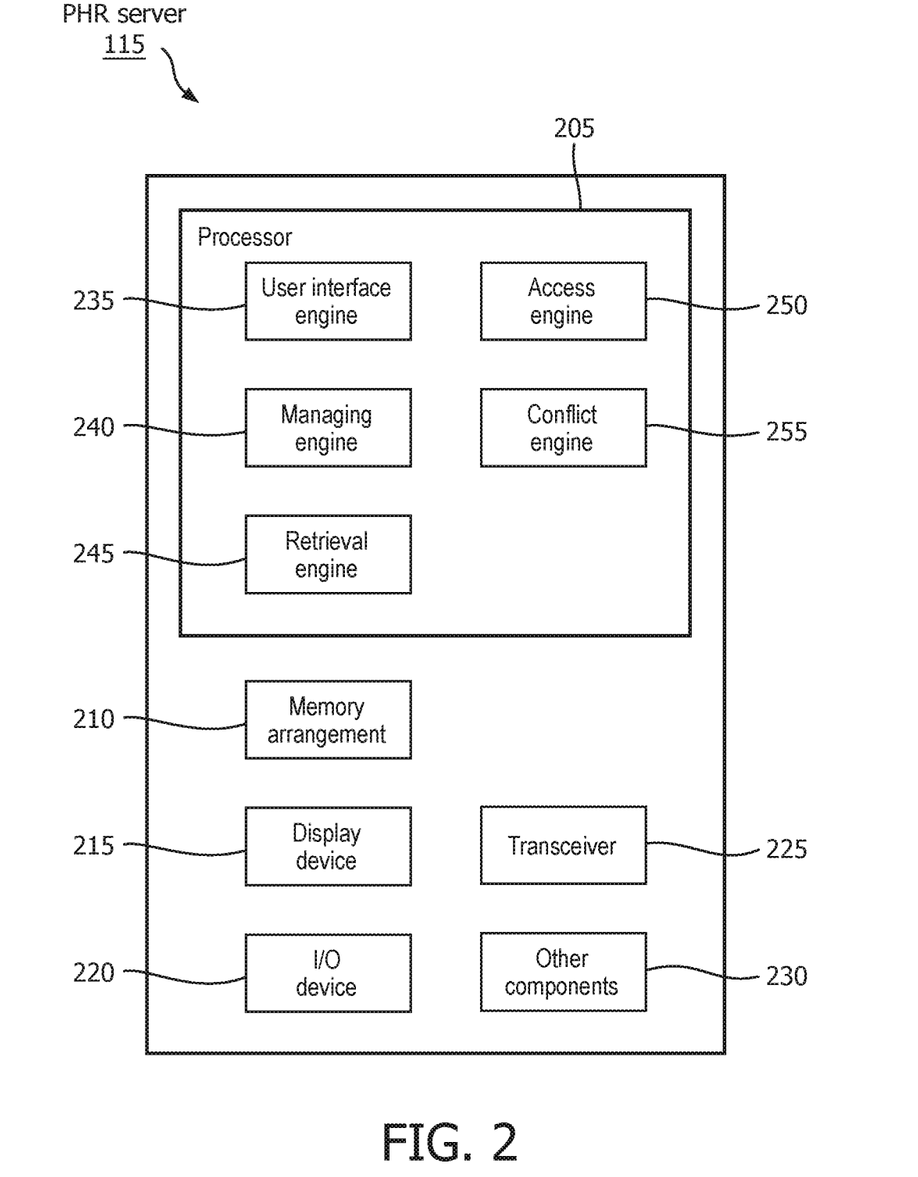
FIG. 2 shows a personal health record server of FIG. 1 according to the exemplary embodiments.

As described above, the PHR server 115 may manage information flow of the PHR for the owner using the user device 105 by processing inputs and requests from the user device 105 as well as the health care entities. FIG. 2 shows the PHR 115 of FIG. 1 according to the exemplary embodiments. The PHR server 115 may provide various functionalities in performing the first and second mechanisms to control the information flow. Although the PHR server 115 is described as a network component (specifically a server), the PHR server 115 may be embodied in a variety of hardware components such as a portable device (e.g., a tablet, a smartphone, a laptop, etc.), a stationary device (e.g., a desktop terminal), incorporated into the user device 105, incorporated into a website service, etc. The PHR server 115 may include a processor 205, a memory arrangement 210, a display device 215, an input and output (I/O) device 220, a transceiver 225, and other components 230 (e.g., an imager, an audio I/O device, a battery, a data acquisition device, ports to electrically connect the PHR server 115 to other electronic devices, etc.).

The processor 205 may be configured to execute a plurality of applications of the PHR server 115. As will be described in further detail below, the processor 205 may utilize a plurality of engines including a user interface engine 235, a managing engine 240, a retrieval engine 245, an access engine 250, and a conflict engine 255. The user interface engine 235 may be configured to generate a user interface upon which the owner using the user device 105 and the health care entities may interact with the PHR server 115. The managing engine 240 may be configured to update the PHR and organize the health related information in the PHR, particularly into a plurality of different sections. The retrieval engine 245 may be configured for the first mechanism to process requests from the user device 105 to retrieve health related information from the health care entities. The access engine 250 may be configured for the second mechanism to process requests from the health care entities for health related information in the PHR. The conflict engine 255 may be configured to determine conflicts in the health related information of the PHR.

It should be noted that the above noted applications and engines each being an application (e.g., a program) executed by the processor 205 is only exemplary. The functionality associated with the applications may also be represented as components of one or more multifunctional programs, a separate incorporated component of the PHR server 115 or may be a modular component coupled to the PHR server 115, e.g., an integrated circuit with or without firmware.

The memory 210 may be a hardware component configured to store data related to operations performed by the PHR server 115. Specifically, the memory 210 may store data received from the user device 105 and the health care entities that is incorporated in the PHR stored in the PHR repository 120. The display device 215 may be a hardware component configured to show data to a user while the I/O device 220 may be a hardware component that enables the user to enter inputs. For example, an administrator of the PHR server 115 may define how the engines 235-255 are to operate using the display device 215 and the I/O device 220. It should be noted that the display device 215 and the I/O device 220 may be separate components or integrated together such as a touchscreen. The transceiver 225 may be a hardware component configured to transmit and/or receive data via the communications network 110.

According to the exemplary embodiments, the PHR server 115 may perform various different operations to manage the flow of information to and from the PHR belonging to the owner using the user device 105. The user interface engine 235 may be configured to generate a user interface upon which the owner using the user device 105 and the health care entities may interact with the PHR server 115. The user interface which is provided and shown on the user device 105 may provide a data sharing application program interface between the user device 105 and the PHR server 115 as well as between the health care entities and the PHR server 115.

The user interface of the user device 105 may display an initial user interface. The initial user interface may include publicly available information regarding the services provided by the PHR server 115, particularly to maintain a PHR. The initial user interface may allow a new user to create an account with the PHR server 115 and create a new PHR. The initial user interface may also provide various terms and conditions associated with using the services of the PHR server 115. As noted above, the exemplary embodiments are described with regard to the PHR server 115 providing the services of maintaining a PHR for the owner using the user device 105. Accordingly, the initial user interface may also allow an already existing user having an account and a PHR using the services of the PHR server 115 to log into the account and the PHR. For example, the owner may use the user device 105 to transmit authentication information to log into the account and access the PHR.

Once the owner has logged into the account, the user interface may provide various displays that allow the owner to view the health related information included in the PHR. For example, health related information may have been requested or included through an automated operation in the PHR. Once the requested health related information has been included, the display may also include this information in the PHR for the owner to view.

The user interface may also allow the owner to provide various other inputs in addition to the inputs used to view the health related information of the PHR. In a first example, the owner may provide an input to update health related information that is read and write capable. For example, the personal information (e.g., contact information, emergency contact information, primary care physician information, etc.) may be changed by the owner. Accordingly, an update input may allow the write capable portions of the PHR to be added, changed, or deleted. The personal information may also include a care plan of the owner of the PHR where the care plan may identify health goals of the owner of the PHR. As will be described in detail below, the PHR server 115 may receive the update input for personal information and update a personal section of the PHR for the owner. The update input may also be used to create health care entity sections. For example, as noted above, the owner using the user device 105 may have a history with the HCPs 125, 135, 145, 150, 155. Accordingly, the update input may be used to create sections for these HCPs or with health care entities such as the HCOs 130, 140 when the HCPs are to be grouped into a common section. As will be described in detail below, the PHR server 115 may receive the update input for health care entity sections and update an aggregated section of the PHR for the owner.

In a second example, the owner may provide an input to request health related information from a health care entity to be retrieved. For example, the owner may have recently had a visit with the HCP 125. The visit may have entailed that a laboratory test is to be performed on a sample that was provided. Accordingly, the owner may provide a corresponding retrieval input to the PHR server 115 indicating that the results of the lab test are to be retrieved and included in the PHR. The owner may provide a similar input for each visit with a HCP. It is again noted that the owner manually providing the retrieval input is only exemplary. The PHR server 115 may provide automated operations for the owner to perform the operations in retrieving information from a health care entity. For example, the owner may have a calendar of visits to a HCP. The PHR server 115 may have access to this calendar and accordingly perform retrieval operations for information associated with past visits. In another example (and as will be described below), the HCP or HCO may manually perform or utilize an automated operation to push information of a visit with the owner of the PHR to the PHR server 115. As will be described in detail below, the requested information from the retrieval input may be incorporated by the PHR server 115 into the aggregated section of the PHR, particularly into a sub-section corresponding to the HCP or HCO from which the requested information originates.

In a third example, the owner may provide an input to add or change a setting associated with a health care entity. Although the health related information in the PHR is owned by the owner using the user device 105, the health care entity may also request to view select portions of the PHR. For example, an upcoming visit with a HCP of the health care entity may require fore knowledge of previous tests and/or procedures. By viewing the corresponding information in the PHR, the HCP may easily receive the requested information. It is again noted that the health care entity is only exemplary and the request to view portions of the PHR may be from the third party device 160. Thus, in anticipation of a request from the HCP, a setting input to change the setting for a specified health care entity may be provided by the owner. The setting input may define which portions of the PHR that may be viewed by the specified health care entity. Specifically, the setting input may indicate access to the aggregated section of the PHR. The setting input may additionally define a duration of time in which the selected portions may be viewed. That is, the specified health care entity may only be allowed to view the selected portions of the PHR for a limited time duration. The setting input may also provide a more general instruction for how the health related information in the PHR may be viewed. For example, portions of the personal information (e.g., name and emergency contact information) may be publicly available for viewing at all times while other portions of the personal information (e.g., address) may be available only to selected health care entities or only to the owner. In this manner, the setting input may further indicate access to other sections of the PHR.

The user interface engine 235 may further be configured to generate user interfaces for the health care entities to provide inputs or requests. As the health care entity does not own the PHR, the inputs that may be provided by the health care entity may be limited. In a first example, if a section for the health care entity is not available in the PHR (e.g., the owner of the PHR never provided the update input to create the section), the health care entity may also provide an update input to create the section (e.g., to push information into this section). However, it is noted that the health care entity may only create its own section in the PHR. That is, the health care entity does not have any capability of affecting the other sections of the PHR. In a second example, the health care entity may request to access health related information in the PHR. In one implementation, the health care entity may also have an account with the service of the PHR server 115. Once logged into the account, the health care entity may provide the appropriate input or request. In a substantially similar manner, the user of the third party device 160 may utilize a substantially similar implementation.

The managing engine 240 may be configured to update the PHR and organize the health related information in the PHR. Initially, the managing engine 240 may associate the PHR with a universally unique identifier (UUID) corresponding to the owner of the PHR (e.g., the user of the user device 105). Thus, information that is received may be associated with the UUID which identifies the owner and the PHR to which the information is to be incorporated. The managing engine 240 may structure the PHR into a plurality of sections. In a first example, the sections may include a user generated data section or a personal section. Specifically, the user generated data section may relate to a section where personal information associated with the owner is included. For example, the managing engine 240 may manually receive the personal information from the owner via the user device 105 or may receive the personal information from other sources (e.g., IoT devices, coaching programs, etc.). The personal information to be included in the PHR may be received using a Fast Healthcare Interoperability Resource (FHIR) and organized as a FHIR data representation.

In a second example, the sections may include an aggregated section in which one or more subsections may respectively correspond to a health care entity. As noted above, health care entity subsections may be created based on the update inputs (from the owner or from the health care entity) for the different health care entities (or HCPs) who have provided health care services for the owner of the PHR. It is noted that the managing engine 240 may enable these sections to be fully accessed by the owner and provide read and write capabilities to the sections. That is, the owner may view the sections, add/update/delete the personal section as well as the information included in the personal section, and add/update/delete the health care entity sections.

Although the health care entity sections are within the control of the owner, the managing engine 240 may limit the capability of the information within the health care entity sections to a read only capability. That is, the owner may be prevented from adding/updating/deleting the information in the health care entity sections. Specifically, the information that is included in the health care entity section may be based on the EHR owned by the corresponding health care entity. For example, the information may be results or a summary of a session of the owner with a HCP. The owner may own the information once included in the PHR and access the information in the read only mode.

The retrieval engine 245 may be configured for the first mechanism to process requests from the user device 105 to retrieve health related information from the health care entities. As noted above, the user interface engine 235 may enable the owner to provide an input to initiate retrieval of information from a health care entity to be included in the PHR. In a particular example, the retrieval engine 245 may generate a request for the health care entity and transmit a message to the health care entity including the request. The request may include instructions on how to push the requested information. For example, if the PHR server 115 is a browser application based service, a hyperlink may be provided that forwards the health care entity to a webpage where a text document may be uploaded. The PHR server 115 may utilize a FHIR API for the requested information to be provided to the PHR server 115 from the health care entity. Subsequently, the retrieval engine 245 may incorporate the information into the PHR in the corresponding health care entity section. Specifically, the retrieval engine 245 may cooperate with the managing engine 240 to incorporate the retrieved information into the aggregated section of the PHR, particularly to the subsection corresponding to the health care entity in the aggregated section of the PHR that provided the retrieved information.

It is noted that the health care entity may also proactively provide the information to the retrieval engine 245. That is, even if the owner has not initiated a retrieval, the health care entity may utilize the service of the PHR server 115. If the health care entity also has an account with the PHR server 115, the health care entity may provide an identifier (e.g., the UUID) of the PHR for the owner (which may be have been volunteered by the owner). Accordingly, the health care entity may upload the information to be included in the PHR.

It is also noted that the health care entity may provide the information based on the EHR with various options. For example, the information may be uploaded with masks. Accordingly, specific clinical data in the uploaded information may be masked so the owner may still own the information but not necessarily have all associated rights or access. That is, the owner may be prevented from viewing the specific clinical data. However, the health care entity may also delegate and share the uploaded information. For example, the owner may be prevented from viewing the specific clinical data or any information that is masked. However, the delegation/sharing by the health care entity may allow other health care entities to view the masked information. In this manner, the managing engine 240 may further utilize a selectively viewable section. More generally, the selectively viewable section may include information that may not be viewed by the owner but exchanged by HCPs, detailed care plans which is viewable by the owner, prescription information, etc. It is noted that the information in the selectively viewable section may be dynamic. For example, the information may be based on in-flight applications (e.g., from a HCP, an ambulatory care team, a coaching plan, a lifestyle plan, etc.).

The access engine 250 may be configured for the second mechanism to process requests from the health care entities (or the third party device 160) for health related information in the PHR. The access engine 250 may utilize the setting input from the user device 105. Accordingly, the access engine 250 may process requests from the health care entities based on the setting input. If the access engine 250 determines that the request is for private information that is inaccessible except to the owner of the PHR, the request may be denied. If the access engine 250 determines that the request is for accessible information, the access engine 250 may continue to process the request. If the request is for publicly available information, the request may be processed and the information may be provided. If the request is not for publicly available information but also not for private information, the access engine 250 may then determine whether the request is from an authorized health care entity. If the request is from an authorized health care entity, the information being requested is then verified to be within the selected portions as identified in the setting input. If the setting input also indicates a time duration of when the selected portion of health related information is accessible by the specified health care entity, the access engine 250 may perform this further verification prior to providing the requested information. In this manner, the access engine 250 may grant the health care entity access to view the requested information (e.g., using the FHIR API when the identification used by the health care entity is associated with the FHIR patient identification and the UUID). It is noted that since the information in the PHR is owned by owner, the health care entity accessing the information may be provided a read only capability.

The conflict engine 255 may be configured to determine conflicts in the health related information of the PHR. The conflict engine 255 may be a further feature provided by the services of the PHR server 115. Specifically, when information in the PHR is changed (e.g., addition, updating, deletion), the conflict engine 255 may determine whether there is a conflict in the most current information of the PHR. For example, an existing prescription may have been prescribed by a first HCP which has been included under a first health care entity section of the PHR. A subsequent prescription may have also been prescribed by a second HCP which has been included under a second health care entity section of the PHR. The conflict engine 255 may generate an alert for the second HCP indicating the conflict which may provide an opportunity for the subsequent prescription to be modified. In another example, a care plan of the owner of the PHR may include losing weight. However, a course of action recommended by a HCP as included in a corresponding health care entity section of the PHR may include medication having a side effect of weight gain. The conflict engine 255 may generate an alert that the course of action runs contrary to the care plan of the owner of the PHR.

The PHR server 115 having the features and functionalities described above provide an operative PHR for the owner. The operative PHR provides various solutions to needs associated with owning, managing, maintaining, and updating the PHR. Specifically, the PHR being maintained with a personal section, an aggregated section, a selectively viewable section, etc. enables the exchange of information in the PHR to be performed in a controlled and flexible manner. For example, the operative PHR according to the exemplary embodiments is cloud based to enable a sharing of the health related information in the PHR for health care entities. In another example, the segmentation of the PHR into specific sections such as the personal section and the health care entity subsections with associated access authorization provides a substantial amount of flexibility in the type of content or information that may be stored and accessed. In a further example, the operative PHR provides a sharing of the health related information in the PHR to the health care entities where the health care entities may be "registered" into the PHR.

Figure 3:
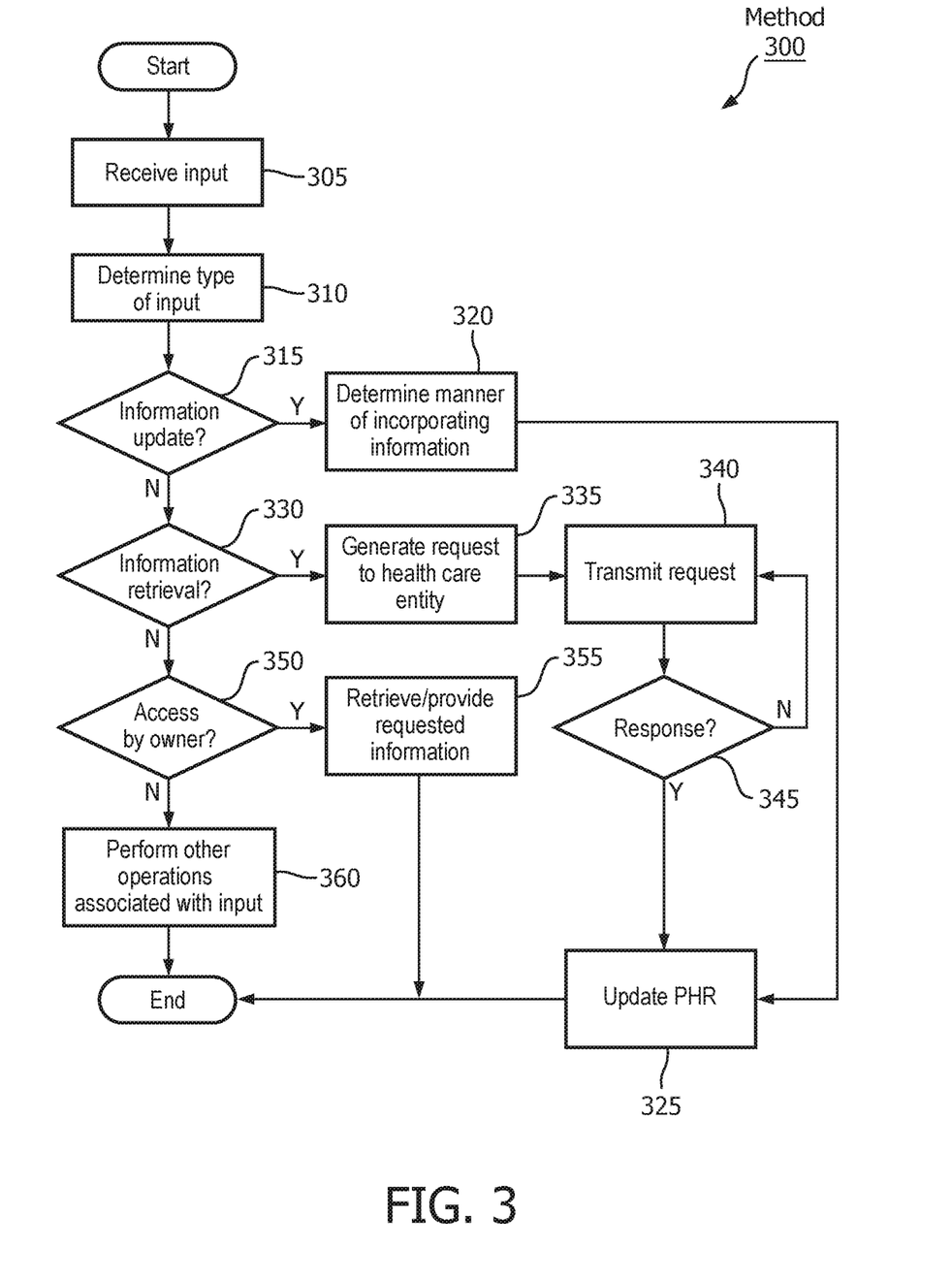
FIG. 3 shows a method for including information in a patient health record according to the exemplary embodiments.

FIG. 3 shows a method 300 for including information in a PHR according to the exemplary embodiments. Specifically, the method 300 may relate to the first mechanism of the exemplary embodiments in which the owner interacts with the PHR server 115 and the health related information of the PHR. Accordingly, the method 300 will be described from the perspective of the PHR server 115. The method 300 will also be described with regard to the system 100 of FIG. 1 and the plurality of engines 235-255 of the PHR server 115 of FIG. 2.

In 305, the PHR server 115 receives an input. For example, the input may be from the user device 105 or from a health care entity. It may be assumed that the owner is an existing user of the services of the PHR server 115 and the owner has a PHR being maintained by the PHR server 115. It may also be assumed that the health care entity may be configured to interact with the PHR server 115 (e.g., through an account of the health care entity for the services of the PHR server 115). As described above, the input from the owner may be related to a variety of different operations. Thus, in 310, the PHR server 115 determines the type of input that was received.

In 315, the PHR server 115 determines if the input is directed to an information update. If the input is an update input, in 320, the PHR server 115 determines the manner of incorporating the information. As the update input relates to a write operation of the PHR, the PHR server 115 may include the information of the update input with a respective operation into the appropriate section. For example, if the update input is an addition, change, or deletion to a personal section having personal information associated with the owner of the PHR, in 325, the PHR server 115 may update the PHR accordingly. In another example, if the update input is an addition, change or deletion to a health care entity subsection associated with a respective health care entity, in 325, the PHR server 115 may update the PHR accordingly. In a further example, if the update input is information to be included to a health care entity subsection, in 325, the PHR server 115 may update the PHR accordingly.

If the input is not an update input, in 330, the PHR server 115 determines if the input is directed to an information retrieval. If the input is a retrieval input, in 335, the PHR server 115 generates a request to the health care entity identified in the retrieval input from which the requested information is to be received. As described above, the owner may have had a visit or session with a HCP in which a summary of the visit and/or results of a test and/or procedure may be tracked (e.g., kept in an EHR of the health care entity). Accordingly, the retrieval input may have indicated the visit with the HCP, an identity of the health care entity corresponding to the HCP, etc. Thus, in 340, the PHR server 115 transmits the request to the health care entity. The health care entity to which the request is transmitted may be part of one or more health care practitioners with whom the owner of the PHR has had experience or visits/sessions. That is, the health care entity may have an EHR being kept for the owner.

In 345, the PHR server 115 determines if a response to the request has been received. Specifically, the PHR server 115 determines if the health care entity has responded by uploading the requested information (e.g., post clinical information). If no response has been received, the PHR server 115 may return to 340 for another request to be transmitted. However, if the response has been received, in 325, the PHR server 115 may update the PHR accordingly. Specifically, the health care entity section may be updated to include the uploaded information.

It is noted that the PHR server 115 may transmit the request based on an identified time or based on an expectation timer. For example, the retrieval input may have indicated when the health care entity will likely have the requested information prepared. Accordingly, the PHR server 115 may transmit the request at this time or at a later time. In another example, the retrieval input may be privy to when the indicated health care entity completes preparation of the EHR for an identified visit/test/procedure. Accordingly, the PHR server 115 may transmit the request based on this expectation timer.

If the input is not a retrieval input, in 350, the PHR server 115 determines if the input is directed to information access by the owner. If the input is an access input by the owner, in 355, the PHR server 115 retrieves and provides the requested information. As the access input is received from the owner of the PHR who has full access to the information in the PHR, no verification procedure may be required. However, as noted above, the information in the health care entity sections may include masked portions which are only viewable by health care entities. Thus, the PHR server 115 may hide these masked portions from being viewed by the owner.

If the input is not an access input, in 360, the PHR server 115 processes whatever request is included in the input. For example, the input may be unrelated to the PHR or may relate to an administrative aspect of the services provided by the PHR server 115. In another example, the PHR server 115 may enable a communication session to be established between the user device 105 and a health care entity.

It is noted that the method 300 and the inputs relate to the owner of the PHR only. However, the method 300 may also include operations associated with the first mechanism when inputs from the health care entity are received. For example, the health care entity may provide an input to create a corresponding health care entity section in the PHR if not already existing. Thus, when the response in 345 is being provided, the health care entity may verify that its health care entity section exists in the PHR and provide this input if not yet present.

Figure 4:
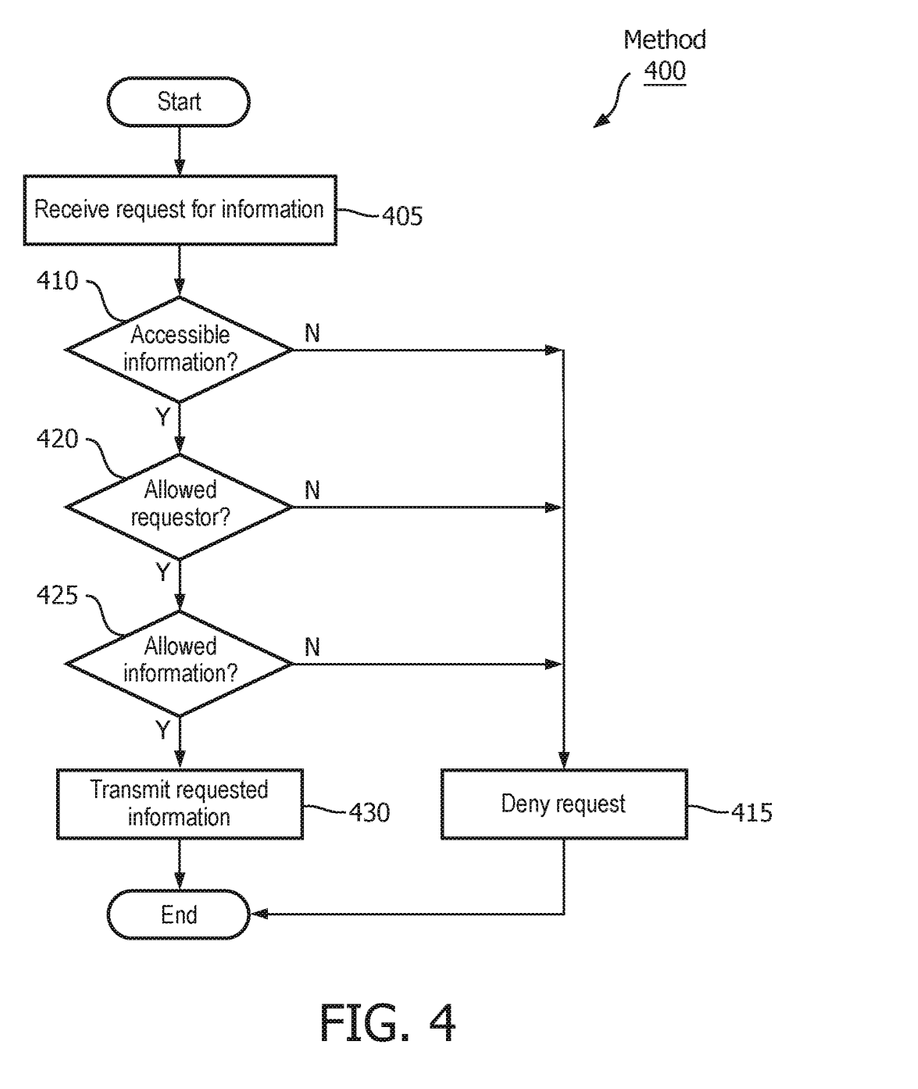
FIG. 4 shows a method for providing information from a patient health record according to the exemplary embodiments.

FIG. 4 shows a method 400 for providing information from a PHR according to the exemplary embodiments. Specifically, the method 400 may relate to the second mechanism of the exemplary embodiments in which health related information from the PHR is requested by a health care entity. Accordingly, the method 400 will be described from the perspective of the PHR server 115. The method 400 will also be described with regard to the system 100 of FIG. 1 and the plurality of engines 235-255 of the PHR server 115 of FIG. 2.

In 405, the PHR server 115 receives a request for information (e.g., from the health care entity or the third party device 160). As noted above, the health care entity may be a HCP or a HCO including one or more HCPs. The health care entity may also require viewing of a portion of the health related information in the PHR (e.g., for an upcoming visit from the owner, to prepare a document for the owner, etc.).

In 410, the PHR server 115 determines if the request from the health care entity is for information in the PHR that is generally accessible. As described above, the PHR may be sectioned into a plurality of sections. The owner of the PHR may provide a setting input that defines which of the health related information in the PHR is to be kept private where only the owner is allowed access to view and/or write. If the request is for inaccessible information, in 415, the PHR server 115 denies the request.

If the request is for accessible information, in 420, the PHR server 115 determines if the requestor transmitting the request is an allowed entity. As described above, an access input from the owner may define identifies of one or more health care entities that may access respective selected portions of the health related information in the PHR. Thus, the PHR server 115 may determine if an identity of the requesting health care entity is included in the access input. The PHR server 115 may also utilize a different standard. For example, if there is a section corresponding to the requesting health care entity, the health care entity may always be allowed access to this section (and this section only unless specified for further access in the access input). If the request is from an unauthorized entity, in 415, the PHR server 115 denies the request.

If the request is from an allowed entity, in 425, the PHR server 115 determines if the portion of the information being requested is allowed to be provided to the requesting health care entity. Again, the access entity may have defined which portions of the health care information in the PHR may be accessed by specified health care entities. Thus, if the request is for unauthorized accessible information, in 415, the PHR server 115 denies the request. However, if the request is for authorized accessible information, in 430, the PHR server 115 transmits the requested information to the health care entity or allows access to view the requested information. It is noted that the health care entity may be provided read only capability.

It is noted that the method 400 may include a further verification operation. As described above, the PHR server 115 may utilize a timing functionality in which an allowed health care entity is permitted to access allowed portions of the health care information in the PHR. Thus, the method 400 may include an operation to determine if the request is received within this defined time period (e.g., as indicated in the access input). If outside this time period, the request may be denied. If within this time period, the request may be processed.

The exemplary embodiments provide a device, system, and method of creating and providing an operative personal health record. The personal health record may include health related information of the owner of the record which is organized according to health care entities. The information may have associated access privileges or settings that allow the user to view the entirety of the information while requesting parties such as health care entities may be granted rights to view selected portions of the information.

The exemplary embodiments utilize a cloud based segmented personal health record with health related information may be shared to authorized entities as selected by the owner. The personal health record may also contain health care entity specific sections used to register these entities and store corresponding health related information from electronic health records owned by the corresponding entity. Through a publicly established application program interface, the PHR may register the health care entity with the personal health record for post clinical data to be included that provides a way for the owner to access this data in the personal health record. The application program interface also allows the owner to list the available health care entities and establish grant privileges to the health related information for viewing.

Those skilled in the art will understand that the above-described exemplary embodiments may be implemented in any suitable software or hardware configuration or combination thereof. An exemplary hardware platform for implementing the exemplary embodiments may include, for example, an Intel x86 based platform with compatible operating system, a Windows platform, a Mac platform and MAC OS, a mobile device having an operating system such as iOS, Android, etc. In a further example, the exemplary embodiments of the above described method may be embodied as a computer program product containing lines of code stored on a computer readable storage medium that may be executed on a processor or microprocessor. The storage medium may be, for example, a local or remote data repository compatible or formatted for use with the above noted operating systems using any storage operation.

It will be apparent to those skilled in the art that various modifications may be made in the present disclosure, without departing from the spirit or the scope of the disclosure. Thus, it is intended that the present disclosure cover modifications and variations of this disclosure provided they come within the scope of the appended claims and their equivalent.

What is claimed is:

1. A method, comprising:
at a personal health record (PHR) server maintaining a PHR of an owner, the PHR including a plurality of sections, one of the sections being an aggregated section including a plurality of subsections, one of the subsections corresponding to a health care entity:
receiving a retrieval input from the owner of the PHR, the retrieval input identifying the health care entity from which information is to be requested;
generating a request for the information;
transmitting the request to the health care entity;
receiving the information from the health care entity;
including the information in the subsection of the aggregated section in the PHR corresponding to the health care entity;
receiving an access input from the owner of the PHR, the access input requesting the PHR server to display the information within a defined time period to permit the health care entity to access the information in the PHR when the request is received within the defined time period;
receiving an update input from one of the owner of the PHR and the health care entity to update the PHR, the update input further instructing the PHR server to create the subsection corresponding to the health care entity in the aggregated section and update the subsection in the PHR corresponding to the health care entity; and
receiving a setting input from the owner of the PHR, the setting input defining an access privilege associated with an entity identity corresponding to the health care entity, the access privilege indicating further subsection in the aggregated section of the PHR, the further subsection corresponding to a further health care entity.

2. The method of claim 1, wherein the information includes masked portions, the masked portions prevented from being displayed to the owner of the PHR.

3. The method of claim 1, further comprising:
associating the PHR to a universally unique identifier corresponding to the owner to the PHR.

4. The method of claim 1, further comprising:
receiving an entity access request from the health care entity;
determining whether the entity access request includes the entity identity;
when the entity access request includes the entity identity, determining whether the entity access request includes an indication for the further subsection; and
when the entity access request includes the indication, providing access to the further subsection in the aggregated section of the PHR.

5. The method of claim 1, further comprising:
determining whether there is a conflict between the information and other information of the PHR; and
when the conflict is determined, generating an alert for the health care entity.

6. The method of claim 1, wherein the PHR is stored in a PHR repository that is a cloud based storage structure.

7. The method of claim 1, wherein the health care entity is one of a health care practitioner or a health care organization including one or more health care practitioners.

8. A personal health record (PHR) server maintaining a PHR of an owner, comprising:
a transceiver communicating via a communications network, the transceiver configured to exchange data with a user device utilized by the owner of the PHR and an electronic device of a health care entity;
a memory storing an executable program; and
a processor that executes the executable program that causes the processor to perform operations in maintaining the PHR, the PHR including a plurality of sections, a first one of the sections being a personal section including personal information associated with the owner, a second one of the sections being an aggregated section including a plurality of subsections, each of the subsections corresponding to a respective health care entity, the subsections including respective health related information associated with the owner based on a respective record maintained by the respective health care entity,
wherein a limited time duration is defined for viewing the first and second one of the sections,
receiving an update input from one of the owner of the PHR and the health care entity to update the PHR, the update input further instructing the PHR server to create the subsection corresponding to the health care entity in the first and second sections and update the first and second sections in the PHR corresponding to the health care entity, and
receiving a setting input from the owner of the PHR, the setting input defining an access privilege associated with an entity identity corresponding to the health care entity, the access privilege indicating further subsection in the aggregated section of the PHR, the further subsection corresponding to a further health care entity.

9. The PHR server of claim 8, wherein the personal information is received from the user device.

10. The PHR server of claim 8, wherein the personal section has a restricted access level preventing the health care entities from viewing the personal information.

11. The PHR server of claim 8, wherein the processor performs operations further comprising generating a request for first health related information, the transceiver further transmitting the request to a first health care entity and receiving the health related information from the first health care entity.

12. The PHR server of claim 11, wherein the processor performs operations further comprising:
   determining an identity of the first health care entity;
   identifying one of the subsections corresponding to the identity; and
   including the first health related information in the subsection corresponding to the identity.

13. The PHR server of claim 8, wherein a third one of the sections is a selectively viewable section including viewable information for selected entities.

14. The PHR server of claim 13, wherein the viewable information is prevented from being viewed by the owner.

15. The PHR server of claim 8, wherein the transceiver receives an access input indicating an identity and a selected subsection of the aggregated section.

16. The PHR server of claim 15, wherein the processor performs operations further comprising:
   receiving an access request from a requestor;
   determining a requesting identity of the requestor;
   when the requesting identity of the requestor corresponds to the identity indicated in the access input, providing access to the requestor to the selected subsection.

17. A personal health record (PHR) server maintaining a PHR of an owner, the PHR including a plurality of sections, one of the sections being an aggregated section including a plurality of subsections, one of the subsections corresponding to a health care entity, comprising:
   a transceiver communicating via a communications network, the transceiver configured to exchange data with a user device utilized by the owner of the PHR and an electronic device of a health care entity;
   a memory storing an executable program; and
   a processor that executes the executable program that causes the processor to perform operations, comprising:
      receiving a retrieval input from the owner of the PHR, the retrieval input identifying the health care entity from which information is to be requested;
      generating a request for the information;
      transmitting the request to the health care entity;
      receiving the information from the health care entity;
      including the information in the subsection of the aggregated section in the PHR corresponding to the health care entity
      receiving an access input from the owner of the PHR, the access input requesting the PHR server to display the information within a defined time period to permit the health care entity to access the information in the PHR when the request is received within the defined time period;
      receiving an update input from one of the owner of the PHR and the health care entity to update the PHR, the update input further instructing the PHR server to create the subsection corresponding to the health care entity in the aggregated section and update the subsection in the PHR corresponding to the health care entity; and
      receiving a setting input from the owner of the PHR, the setting input defining an access privilege associated with an entity identity corresponding to the health care entity, the access privilege indicating further subsection in the aggregated section of the PHR, the further subsection corresponding to a further health care entity.

\* \* \* \* \*